(12) United States Patent
Andreu Morales et al.

(10) Patent No.: US 7,476,511 B2
(45) Date of Patent: Jan. 13, 2009

(54) METHOD OF DETECTING AND ANALYZING PACLITAXEL-MIMETIC COMPOUNDS

(75) Inventors: José Manuel Andreu Morales, Madrid (ES); José Fernando Díaz Pereira, Madrid (ES); María Isabel Barasoain Blasco, Madrid (ES)

(73) Assignee: Jose Manuel Andreu Morales (ES)

( * ) Notice: Subject to any disclaimer, the term of this patent is extended or adjusted under 35 U.S.C. 154(b) by 353 days.

(21) Appl. No.: 10/761,150

(22) Filed: Jan. 20, 2004

(65) Prior Publication Data

US 2004/0203082 A1 Oct. 14, 2004

Related U.S. Application Data

(63) Continuation of application No. PCT/ES02/00262, filed on May 31, 2002.

(30) Foreign Application Priority Data

Jul. 20, 2001 (ES) .............................. 200101710

(51) Int. Cl.
G01N 33/567 (2006.01)
G01N 1/30 (2006.01)
(52) U.S. Cl. .................... 435/7.21; 435/40.5
(58) Field of Classification Search ................ 435/7.23, 435/7.21
See application file for complete search history.

(56) References Cited

U.S. PATENT DOCUMENTS 5,340,724 A 8/1994 Abraham

FOREIGN PATENT DOCUMENTS

| WO | WO 94/20134 | 9/1994 |
|----|-------------|--------|
| WO | WO 97/19938 | 6/1997 |
| WO | WO 99/53295 | 10/1999 |
| WO | WO 00/56894 | 9/2000 |

OTHER PUBLICATIONS

Diaz et al. (J. Biol. Chem. 2000; 275: 26265-26276).*
Andreu et al. (Biochemistry 2001; 40: 11975-11984).*
Andreu, J.M., et al. The Interaction of Baccatin III with the Taxol Binding Site of Microtubules Determined by a Homogeneous Assay with Fluorescent Taxoid Biochemistry 2001; vol. 40 pp. 11975-11984.

JoséFernando Díaz et al., Biochemistry; 32:2747-2755 (1993).
Daniel M. Bollag et al., Cancer Research; 55:2325-2333 (Jun. 1, 1995).
Miguel Abal et al., Cell Motility and the Cytoskeleton, 49:1-15 (2001).
Jose M. Andreu et al., Biochemistry, 37:8356-8368 (1998).
C. Bicamumpaka et al., Journal of Immunological Methods, 212:1-7 (1998).
J. Fernando Díaz et al., The Journal of Biological Chemistry, 275(No. 34): 26265-26276 (Aug. 25, 2000).
Juan A. Evangelio et al., Cell Motility and the Cytoskeleton, 39:73-90 (1998).
Paul G. Grothaus et al., Journal of Natural Products, 58(No. 7): 1004-1014 (1995).
Yi Han et al., Biochemistry. 35:14173-14183 (1996).
Jesús Jiménez-Barbero et al., Bioorganic & Medicinal Chemistry, 6:1857-1863 (1998).
Mary Ann Jordan et al., Current Opinion in Cell Biology, 10:123-130 (1998).
Joseph R. Lakowicz, Principles of Fluorescence Spectroscopy, Second Edition, (1999), pp. xiii-xxiii; 1 and 698.
Yankun Li et al., Biochemistry, 39:616-623 (2000).
Byron H. Long et al., Cancer Research, 58:1111-1115 (Mar. 15, 1998).
Thomas U. Mayer et al., Science, 286:971-974 (Oct. 29, 1999).
F. Javier Medrano et al., Biochemistry, 30:3770-3777 (1991).
Susan L. Mooberry et al., Cancer Research, 59:653-660 (Feb. 1, 1999).
Eva Nogales, Annun. Rev. Biochem., 69:277-302 (2000).
Eva Nogales, Cell, 96:79-88 (Jan. 8, 1999).
Eva Nogales et al., Nature, 391:199-203 (Jan. 8, 1998).
Kevin P. O'Boyle et al., Cancer, 79(No. 5): 1022-1030 (Mar. 1, 1997).
Jerome Parness et al., The Journal of Cell Biology, 91:479-487 (Nov. 1981).
André A. Souto et al., Angew. Chem. Intl. Ed. Engl., 34(No. 23/24):2710-2712 (1995).
Ernst ter Haar et al., Biochemistry, 35:243-250 (1996).

* cited by examiner

*Primary Examiner*—Brandon J Fetterolf
(74) *Attorney, Agent, or Firm*—Klauber & Jackson, LLC

(57) ABSTRACT

A large part of cytostatics, among them paclitaxel (Taxol®) and other recently discovered substances that mimic its anti-tumour effects, have cellular microtubules as their target. The present invention is a high-efficiency homogeneous test based on the use of stabilised microtubules and fluorescent taxoids for detecting any substances that can substitute paclitaxel in its binding site in microtubules, and constituting potentially anticancerous agents.

11 Claims, 2 Drawing Sheets

Figure 1:

1 Taxol   2 baccatine III   3 methyl ester of the side chain on C-13

METHOD OF DETECTING AND ANALYZING PACLITAXEL-MIMETIC COMPOUNDS

RELATED APPLICATIONS

The present application is a Continuation of co-pending PCT Application No. PCT/ES02/00262, filed May 31, 2002, which in turn, claims priority from Spanish Application Ser. No. 200101710, filed Jul. 20, 2001. Applicants claim the benefits of 35 U.S.C. §120 as to the PCT application and priority under 35 U.S.C. §119 as to said Spanish application, and the entire disclosures of both applications are incorporated herein by reference in their entireties.

FIELD OF THE INVENTION

Pharmaceutical sector. Antitumour agents. High-efficiency homogeneous test for the detection of substances that can substitute paclitaxel in its binding site in microtubules and therefore with potential activity as antitumour agents.

DESCRIPTION OF THE ART

Paclitaxel (Taxol®), a compound much used in chemotherapy of cancer, displays side effects just as other anticancer agents do. This diterpenoid compound was originally extracted from the bark of a plant, *Taxus brevifolia*, a slow-growing species which entailed a problem of the lack of a cheap and available source of paclitaxel. The paclitaxel currently used is a semi-synthetic product starting from a precursor extracted from the leaves of yew trees. Moreover, paclitaxel displays problems of extreme insolubility. So, although paclitaxel is a chemotherapy agent with considerable biological activity, the discovery of new sources of paclitaxel or of mimetic compounds of paclitaxel has a decisive utility.

Paclitaxel promotes the assembly of αβ-tubulin in microtubules by preferential binding to assembled tubulin rather than to unassembled tubulin. Its effect is related to that of the GTP nucleotide, with important differences. The GTP binds to one end of the tubulin dimer making contact with the following dimer along each protofilament forming the microtubule, while the paclitaxel binds to one side of the of β-tubulin close to the contact with the following protofilament; in the α-tubulin, the zone corresponding to the binding cavity to paclitaxel is occupied by a loop of the peptide chain (Nogales, E.). The unassembled tubular dimers bind the GTP and the binding site is hidden by the assemblage; while the binding site to paclitaxel exists only in assembled tubulin. The hydrolysis of GTP permits disassemblage and regulation of the microtubules systems. Nevertheless, the activation of the tubulin by paclitaxel is permanent stabilising the microtubules.

The suppression of the dynamics of cellular microtubules by paclitaxel is a primary cause of the inhibition of cell division and of the death of tumour cells (Jordan, M. A. and Wilson., L.). A number of different natural substances, including epotilones (Bollag, D. M., et al.), discodermolide (Ter Haar, E., et al.), eleuterobine (Long, B. H. et al.) and laulimalide (Mooberry, S. I., et al.) imitate the cytotoxic effects of paclitaxel, apparently becoming bound to its site in the microtubules. Each of these substances was discovered by means of different tests for activities similar to that of paclitaxel.

Some patents describe methods for identifying compounds with activities similar to that of paclitaxel. The American U.S. Pat. No. 5,340,724 (Upjohn Co.) describes a method of using paclitaxel-dependent cells (Tax 2-4 CHO) and detecting their growth. The application PCT WO9420134 (Columbia University) provides two monoclonal antibodies produced by two hybridomas which are capable of becoming bound to paclitaxel and to its analogues, as well as their use for determining the presence and quantity of paclitaxel or its biologically active derivatives. Another patent application, PCT WO0056894 (Cytoclonal pharmaceutics, Inc.), describes the DNA sequences that code the beta tubulin of different species of fungi of the genus *Pestalotiopsis;* these purified DNA segments are used for detecting compounds with antitumour activity. Another application, PCT WO 9953295 (California University), consists of a method for the detection of agents that modulate the depolymerisation of microtubules, bringing into contact polymerised microtubules, a protein which depolymerises them and the substances to be tested in the presence of ATP or GTP and detecting the formation of monomers, dimers or oligomers of tubulin by means of different methods such as change of fluorescence (DAPI), centrifugation, etc.

Nevertheless, in contrast with other important biological targets, so far there has not been any standard test for directly detecting and measuring other any ligands capable of replacing paclitaxel in its binding site in the microtubules.

Methods based on luminescence are very useful for these purposes. Fluorescent, hydrosoluble and active derivatives of paclitaxel, bound to an intermediate of alanine in the non-essential position 7 (Souto, A. A., et al.) are specific probes for the binding site of paclitaxel to microtubules (Evangelio, J. A., et al.). These fluorescent taxoids have mainly been used for localising subcellular binding sites of cytotoxic taxoid to microtubules of the pole of the spindle and to centrosomes (Abal, M. A. et al.), as well as for measuring the fast kinetics of binding and of dissociation of the paclitaxel site exposed in microtubules (Diaz, J. F et al.).

SUMMARY OF THE INVENTION

The primary objective of this invention is the development of a homogeneous fluorescent test of ligand binding to the paclitaxel site in microtubules, which permits high-efficiency detection of new paclitaxel mimetics. The method is based upon the combination of two components, a target and a probe. The target consists of microtubules assembled in vitro, which are stabilised by means of chemical cross-linking and conserved in liquid nitrogen. This conservation method is novel. Fluorescent derivatives of paclitaxel, which are specifically bound to the microtubules (patents ES-2121549, ES-2105983, WO-9719938, Consejo Superior de Investigaciones Científicas) (Diaz, J. F., et al.) are used as probe.

The applications of this method are: search for new antitumour agents starting from libraries of natural and synthetic extracts and compounds; evaluation of chemical modifications of series of existing compounds (including paclitaxel, epotilone, discodermolide, euterobine, laulimalide); valuation of content in active taxanes in natural sources; biological and oncological research.

DESCRIPTION OF THE INVENTION

Brief Description Of The Invention

The binding site of microtubules to paclitaxel also binds other recently discovered ligands having antitumour activity.

In the present invention, a high-efficiency homogeneous test has been designed for the detection of paclitaxel biomimetics based on the displacement of the fluorescent taxoid 7-O-[N-(2,7-difluoro-4'-fluoresceincarbonyl)-L-alanyl]paclitaxel of its binding site in diluted solutions of conserved microtubules.

The detection method object of the present invention, and which is claimed, is based on the combination of the two components, the target, which consists of microtubules assembled in vitro, which are stabilised by means of chemical cross-linking and conserved indefinitely frozen in liquid nitrogen until they are used, this method of conserving the microtubules also being claimed in the present invention, and the probe, which consists of the said fluoresceinated derivative of paclitaxel, which is specifically bound to the microtubules.

The method consists of the addition of the substances (non-fluorescent) to test to multiple aliquots of a diluted solution of the target and the probe in multi-well microplates. The substances to test can be compounds of the families of discodermolide, eleuterobine, sarcodicitine, epotilone and paclitaxel. This method can also have application for measuring active paclitaxel-type contents of natural sources and for the high-efficiency detection of new biomimetics of paclitaxel.

The probe bound to the target possesses a much greater fluorescence anisotropy value than that of the free probe; displacement by any competitor substances of the interaction of the probe (reference ligand) with the target is detected by means of the drop in fluorescence anisotropy of the probe with a fluorescence polarisation microplate reader. Alternatively, use is made of the drop in resonance energy transfer (RET) of the probe bound to a rhodaminated acceptor ligand, 7-O-[N-(4'-tetramethylrhodamine-carbonyl)-L-alanyl]paclitaxel or the change in intensity of fluorescence of the probe 7-O-[N-(4'-fluoresceincarbonyl)-L-alanyl]paclitaxel. This method has application in the development of tools for conducting tests in oncological and/or biological research.

Also an object of the present invention is the method for conserving the microtubules indefinitely. This method consists of dialysing the cross-linked microtubules against a conservation buffer and cryopreserving them.

DETAILED DESCRIPTION OF THE INVENTION

With the aim of establishing an effective test of competition based on fluorescence for the binding of ligand to the paclitaxel site in microtubules, the changes in the fluorescent properties of the probe 7-O-[N-(2,7-difluoro-4'-fluoresceincarbonyl)-L-alanyl]paclitaxel (Flutax-2; 10) on the specific binding to microtubules were investigated. Flutax-2 was preferred to the analogous Flutax-1 with non-fluorated fluorescein, for its superior photostability and acid pK (making the di-anion strongly fluorescent at neutral pH values). Methods of fluorescence anisotropy and of resonance energy transfer (RET) were investigated, along with methods of emission intensity (with Flutax-1). Since the microtubules are bound to paclitaxel and to Flutax with great affinity, low concentrations of binding sites were necessary in order to detect competitors of lower affinity. These binding sites, stabilised by dilution, were provided by gently cross-linked microtubules (see for example: Evangelio, J. A. et al.; Diaz, J. F. et al.)

Validation of the Probe and Target. A) Measurement of the Specific Binding of Flutax-2 to Microtubules by Means of Fluorescence Anisotropy and its Cancellation by Paclitaxel The intensity of fluorescence of Flutax-2 changes very little with the binding to microtubules. There is a small change in the excitation maximum from 494 nm to 495 nm (isosbestic point at 500 nm) and a blue shift in emission from 523 nm to 520 nm (not shown here; isosbestic point at 525 nm; Diaz, J. F. et al.). Nevertheless, the fluorescence polarisation of Flutax-2 increases significantly as a result of the binding. The excitation anisotropy spectrum of a 50 nM solution of microtubule sites/Flutax-2 was compared with the spectrum of a similar solution in which the binding sites were blocked by an excess of paclitaxel and of free Flutax-2. Both the negative anisotropy of the 329 nm band and the positive anisotropy of the lower energy excitation transition (495 nm) of the difluoro-fluorescein are specifically increased by the binding of Flutax-2 to microtubules. The anisotropy values determined for the 495 nm band (emission 520 nm; GAB buffer containing glycerol, 25° C.) were: free Flutax-2 (50 nm), $r_{min}$=0.055; in the presence of microtubules blocked with paclitaxel, r=0.060; Flutax-2 specifically bound to the microtubules, $r_{max}$=0.29 (the last was determined by valuation of 50 nm Flutax-2 with growing concentrations of microtubules). These changes are consistent with a strong immobilisation of the fluorophore by the binding. In addition to the anchorage of Flutax-2 via its paclitaxel residue, an interaction of the fluorescein di-anion with a cation residue of microtubules, possibly Arg 282 of β-tubulin, has also been proposed (Evangelio, J. A., et al., see FIG. 10 in Diaz, J. F. et al.).

A binding isotherm of Flutax-2 to microtubules, determined on the basis of the change of anisotropy of the ligand, indicates an equilibrium constant of the binding with value $K_b$=11.5±0.4×10$^8$ M$^{-1}$ in GAB-GDP buffer at 25° C. (this is not significantly different from the values previously obtained by centrifugation (Diaz, J. F., et al.)). The binding of Flutax-2 at these concentrations is entirely annulled by 10 μM paclitaxel.

On the basis of these results, of the observation of the capacity of Flutax-2 to substitute $^3$H-paclitaxel in its binding site, and of the previous results discussed in a detailed kinetic study (Diaz, J. F. et al.), Flutax-2 can be considered a genuine probe for the paclitaxel binding site of microtubules.

Validation of the Probe and Target. B) Detection of the Binding of Flutax-2 to Microtubules by Means of Energy Transfer (RET) to Another Fluorescent Taxoid and its Cancellation by Paclitaxel The closest distances between binding sites to paclitaxel in β-tubulin sub-units of microtubules are ca. 5.5, 8 and 9.5 nm (Nogales, E. et al.), an appropriate interval of distance for RET from fluorescein to fluorophores of rhodamine. The displacement of the donor or acceptor from its binding sites by another non-fluorescent ligand would suppress emission by the acceptor due to excitation of the donor. The emission spectrum (excitation at 460 nm) of binding sites of 50 nM microtubules with 10 nM Flutax-2 and 40 nM Rotax (7-O-[N-(4'-tetramethylrhodamine-carbonyl)-L-alanyl]paclitaxel (Evangelio, A. A. et al.) showed a sensitised emission peak of Rotax, as well as emission of Flutax-2. When the binding sites were blocked with paclitaxel, the emission of fluorescein increased (it did not go out) and changed from 521 to 524 nm, while the contribution of rhodamine fell to a level (a shoulder) similar to that of the non-sensitised emission of Rotax at 582 nm. This experiment indicated the possibility of detecting a ligand binding to the paclitaxel site by the drop in RET.

Validation of the Probe and Target. C) Detection of the Binding of Flutax-1 to Microtubules by Means of Energy Transfer (RET) to Another Fluorescent Taxoid and its Cancellation by Paclitaxel Using Flutax-1 it is possible to characterise the displacement by variation of the intensity of fluorescence.

Fluorescent Test for Detection and Evaluation of Ligands Interacting with the Binding Site of Paclitaxel in Microtubules Using Flutax-2 as a reference probe for the binding site to paclitaxel, the binding of other non-fluorescent ligands which displace Flutax-2 from the microtubules (see FIG. 1) can easily be measured by the changes in their own fluorescence properties in a competition test. The change of fluorescence anisotropy, which was analysed in 96-well plates with a microplate reader, was used. FIG. 2 shows how the paclitaxel and the docetaxel effectively decrease the fluorescence anisotropy of solutions of 50 nM Flutax-2/50 nM microtubule sites. The numerical analysis of the displacement isotherms (see example) indicated that paclitaxel and docetaxel bind to microtubules with equilibrium binding constants of $(3.7\pm1.5)\times10^7$ $M^{-1}$ (four determinations) and $(6.0\pm2.3)\times10^7$ $M^{-1}$ (two determinations), respectively, at 25° C. The ratio of affinities of docetaxel to paclitaxel was $2.7\pm0.3$ on the basis of the individual experiments. An affinity of docetaxel twice that of paclitaxel is in accordance with a previous direct determination (Diaz J. F and Andreu, J. M.). The affinity of paclitaxel is of the same order of magnitude as the values previously determined for paclitaxel (Parness J and Horwitz, S. B.), 2-dibenzoyl-2-(m-aminobenzoyl) paclitaxel (Han, Y. et al.) and 3'-N-m-aminobenzamide-3'-N-debenzamide-paclitaxel (Li, Y. et al.). Baccatine III, so far generally considered to be an inactive compound, entirely inhibited the anisotropy of microtubule Flutax-2, though at total concentrations approximately 200 times greater than paclitaxel (see FIG. 1). The analysis of the displacement data indicated that baccatine III is recognised by the paclitaxel binding site of microtubules with an equilibrium constant of $1.5\pm0.5)\times10^5$ $M^{-1}$ (seven determinations). Baccatine III is equivalent to the taxane ring system, in which the group C-13 OH substitutes the paclitaxel side chain (see chemical structures in FIG. 2). The C-13 side chain has previously been considered as an essential determinant for recognition of paclitaxel. Nevertheless, the methyl ester of the C-13 side chain was, within the limits of its solubility, inactive for displacing Flutax-2. The results indicated an equilibrium constant of less than $=10^3$ $M^{-1}$ for this analogue of the C-13 side chain separated from the rest of the molecule (see FIG. 2.2, determinations).

In a series of control measurements, the displacement of the interaction of $^3$H-paclitaxel with microtubules by baccatine III and Flutax-2 was evidenced by sedimentation and scintillation count. The results of these measurements (see Example) were compatible with those of fluorescence anisotropy tests, except for an apparent affinity of Flutax-2 seven times lower. This confirmed that baccatine III is recognised by the paclitaxel binding site of microtubules. Nevertheless, with the aim of having the majority of the radioactive $^3$H-paclitaxel tracer in solution, instead of being absorbed into the polycarbonate tube of the table-top ultracentrifuge, it was necessary to include 1 mg mL$^{-1}$ of bovine serum albumin, which binds the paclitaxel (keeping it available for interaction with the microtubules) and also the Flutax-2 (decreasing its apparent affinity). These adsorption processes make it impossible to have any direct rigorous measurement of the affinity of the binding of paclitaxel to microtubules in our hands, and therefore of the affinity of its competitors using paclitaxel as a reference ligand in these diluted tests. The additional disadvantages of the binding tests of $^3$H-paclitaxel in comparison with the homogeneous test of the anisotropy of fluorescent taxoid are the operations of centrifugation, separation and radioactive measurement that are required.

Use of the Fluorescence Anisotropy Test in Microplate in Comparison with Other Methods for Mimetic Detection of Paclitaxel The fluorescence method for the detection of binding of ligands to the paclitaxel site of microtubules developed in this work constitutes a first homogeneous test for any other substance acting on this important antitumour target. Its simplicity compares favourably with screening methods based on the stabilisation of microtubules (Bollag, D. M., et al., www.cytoskeleton.com) and with the competitive tests using radioactively marked paclitaxel (above, Bollag, D. M. et al., Diaz, J. F. and Andreu, J. M.). The specific monoclonal antibodies of taxane offer a possibly unsurpassable sensitivity for the determination of drug contents and closely related compounds (Grothaus, P. G. et al; O'Boyle, K. P.; Bicamumpaka, C and Page, M.), nevertheless, they can fail to recognise ligands that are not chemically related to the paclitaxel binding site of the microtubule. Since multiple samples can be easily analysed with the method of polarisation by fluorescence, this test constitutes a useful tool for the evaluation of the affinity of binding of recently designed compounds of the families of discodermolide, eleuterobine, epotilones and paclitaxel. It is also applicable to the measurement of paclitaxel-type active contents of natural sources, and for the high-efficiency investigation of new biomimetics of paclitaxel, in a complementary mode to the cellular explorations for mitotic inhibitors, like those used in the discovery of monastrol (Mayer, T. U. et al.). An interesting property of the fluorescence anisotropy test is its sensitivity for the detection of ligands of medium affinity. This is possible due to the combination of a highly fluorescent taxoid (Flutax-2) with stabilised microtubules, permitting the considerable dilution needed for the effective displacement of the probe through the weakest ligands, which would otherwise not be detected. An example is the detection of baccatine III binding, which provides a new view of the molecular recognition of paclitaxel by microtubules.

BIBLIOGRAPHY

Abal, M. A., Souto, A. A.; Amat-Guerri, F., Acuña, A. U., Andreu, J. M. and Barasoain (2001) *Cell Motil. Cytosk.* 49, 1-15.

Andreu, J. M., Perez-Ramirez, B., Gorbunoff, M. J., Ayala, D. and Timasheff, S. N. (1998) *Biochemistry* 37, 8356-8368.

Bicamumpaka, C. and Page, M. (1998) *J. Immunol. Meth.* 212, 1-7.

Bollag, D. M., McQueney, P. A., Zhu, J., Henses, O., Koupal, L., Liesch, J., Goetz, M., Diaz, J. F. and Andreu, J. M. (1993) *Biochemistry*, 32, 2747-2755.

Diaz, J. F., Strobe, R., Engelborghs, Y., Souto, A. A. and Andreu, J. M. (2000) *J. Biol. Chem.* 275, 26265-26276.

Evangelio, J. A., Abal, M., Barasoain, I., Souto, A. A., Lillo, M. P., Acuña, A. U., Amat-Guerri, F. and Andreu, J. M. (1998) *Cell Motil. Cytoskel.* 39, 73-90.

Grothaus, P. G., Bignami, G. S., O'Malley, S., Harada, K. E., Byrnes, J. B., Waller, D. F., Raybould, T. J., McGuire, M. T. and Alvarado, B. (1995) *J. Nat. Prod.* 58, 1003-1014.

Han, Y., Chaudhary, A. G., Chordia, M. D., Sackett, D. L., Perez-Ramirez, B., Kingston, D. G. and Bane, S. (1995) *Biochemistry* 35, 14173-14183.

Jiminez-Barbero, J., Souto, A. A., Abal, M., Barasoain, I., Evangelio, J. A., Acuña, A. U. Andreu, J. M. and Amat-Guerri, F. (1998) *Bioorg., Med. Chem.* 6, 1857-1863.

Jordan, M. A. and Wilson, L. (1998) *Curr. Opin. Cell Biol.* 10, 123-130.

Lackowitz, J. R. (1999) Principles of fluorescence spectroscopy. Kluwer/Plenum, New York, N.Y. Li, Y, Edsall, R. Jr., Jagtap, P. G., Kingston, D. G. I. and Bane, S. (2000) *Biochemistry* 39, 616-623.

Long, B. H., Carboni, J. M., Wasserman, A. J., Cornell, L. A., Casazza, A. M., Jensen, P. R., Lindel, T., Fenical, W. and Fairchild, C. R. (1998) *Cancer Res.* 58, 1111-1115.

Mayer, T. U., Kapoor, T. M., Haggarty, S. J., King, R. W., Schreiber, S. L., and Mitchison, T. J. (1999) *Science* 286, 971-974.

Medrano, F. J., Andreu, J. M., Gorbunoff, M. J. and Timasheff, S. N. (1991) *Biochemistry* 30, 3770-3777.

Mooberry, S. I. Tien, G., Hernandez, A. H., Plubrukam, A. and Davidson, B. S. (1999) *Cancer Res.* 59, 653-660.

Nogales, E (2000) *Annu. Rev. Biochem.* 69, 277-302.

Nogales, E., Whittaker, M., Milligan, R. A. and Downing, K. H. (1999) *Cell,* 96, 79-88.

Nogales, E., Wolf, S. G. and Downing, K. (1998) *Nature* 391, 199-203.

O'Boyle, K. P., Wang, Y, Schwarz, E. L., Regl, D. L., Eizig, A., Dutcher, J. P., Wiernik, P. H. and Horwitz, S. B. (1997) *Cancer* 79, 1022-1030.

Parness, J. and Horwitz, S. B. (1981) *J. Cell Biol.* 91, 479-487.

Souto, A. A., Acuña, A. U., Andreu, M. J., Barasoain, I., Abal, M. and Amat-Guerri, F. (1995) *Angew. Chem. Ind. Ed. Engl.* 34, 2710-2712.

Ter Haar, E., Kowalsky, R. J., Lin, C. M., Longley, R. E., Gunasekera, S. P., Rosenkrantz, H. S. and Day, B. W. (1996) *Biochemistry* 35, 243-250.

DETAILED DESCRIPTION OF THE FIGURES

Figure 2:
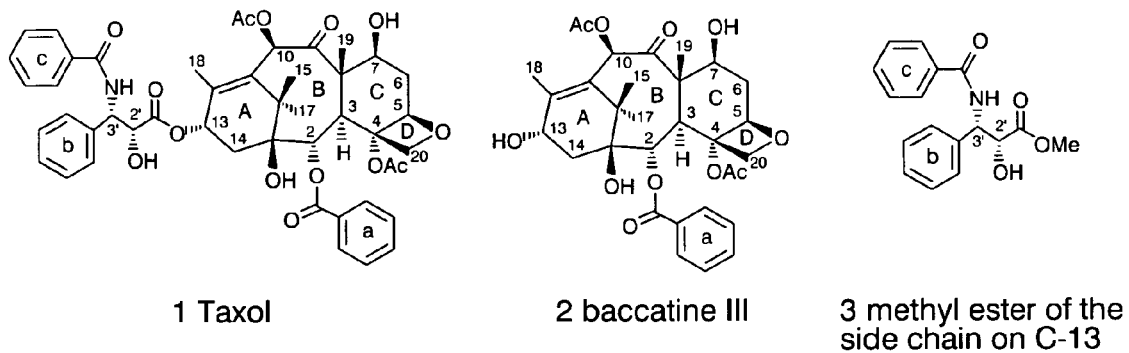
Figure 2:
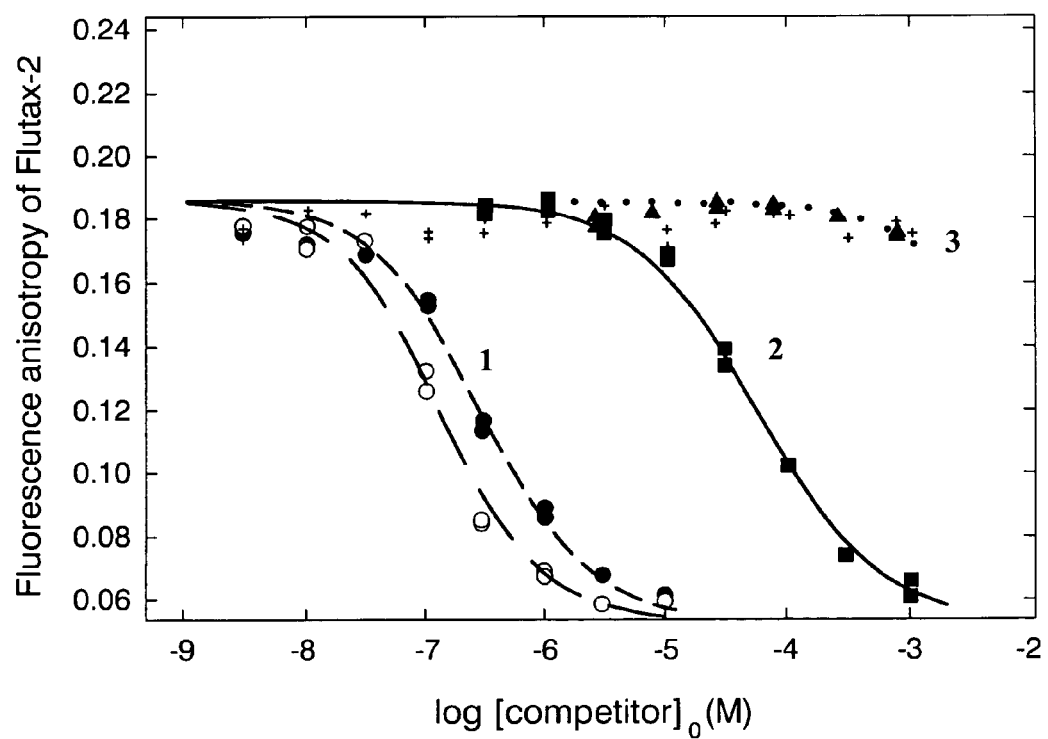

FIG. 1. A fluorescence micrograph of a typical reaction mixture used in this invention, which consists of stabilised microtubules (taxoid sites 100 nM) and Flutax-2 fluorescent taxoid (100 nM). The bar indicates 10 μm.

FIG. 2. Competition isotherms of ligands bound to the paclitaxel site of microtubules in GAB-GDP buffer at 25° C. The fluorescence anisotropy of multiple solutions of 50 nM Flutax-2 and binding sites of 50 nM microtubules with various concentrations of competitors were measured in duplicate, using a microplate reader. The solid circles, paclitaxel (1); the empty circles, docetaxel; and the squares, baccatine III (2); and triangles, methyl ester of the C-13 side chain of paclitaxel (3); the crosses, controls corresponding to DMSO 1% (v/v) without ligand. In this test, each competition curve starts with an anisotropy value corresponding to two thirds of bound Flutax-2 molecules, which are progressively reduced by the competitor that substitutes Flutax-2 in the binding sites. The equilibrium binding constant of Flutax-2 is $1.5 \times 10^8$ $M^{-1}$.

The lines 1 (short broken) and 2 (continuous) correspond to best fits for the binding of paclitaxel and baccatine to the same site with equilibrium constant values of $K=3.2 \times 10^7$ $M^{-1}$ and $K=1.5 \times 10^5$ $M^{-1}$, respectively; the long broken line is the fit of the data for docetaxel, $K=8 \times 10^7$ $M^{-1}$; the line of points passing through the data for the side chain methyl ester is a simulation of a binding of low affinity binding with $K=7 \times 10^2$ $M^{-1}$ (observe that these last data are similar to those for the controls).

EXAMPLE OF EMBODIMENT OF THE INVENTION

1. Taxoids. Fluorescent Probe

Standard concentrated solutions were prepared and were kept at −20° C. in a dry atmosphere. The paclitaxel (from the National Cancer Institute, Bethesda, Md.) was measured spectroscopically at 273 nm following dilution in methanol, using an extinction coefficient of 1,700 $M^{-1}$ $cm^{-1}$ (Diaz, J. F. and Andreu, J. M.) $^3$H-paclitaxel (4 Ci mmol$^{-1}$) was obtained from Moravek Biochemicals (Brea, Calif.), Docetaxel (Taxotere) was supplied by Rhône-Poulenc Rorer (Antony, France). Baccatine III was obtained from Sigma; it was found to be free of impurities by means of HPLC (a 20-80% gradient of acetonitrile in 0.05% of aqueous trifluoroacetic acid in a C-18 column, monitored at 228 nm). An extinction coefficient of baccatine III determined approximately was 900±100 $M^{-1}$ $cm^{-1}$ (273 nm, methanol). Baccatine III was soluble at the concentrations used in 10 mM sodium phosphate, 1 mM ethyleneglycol bis (β-aminoethylether)-N,N,N',N'-tetracetic acid (EGTA), 0.1 mM GTP, 6 mM $MgCl_2$, 3.4 M glycerol, (GAB buffer) pH 6.5 with DMSO at 1%. The methyl ester of the C-13 side chain of paclitaxel was supplied by E. Baloglu and D. G. I. Kingston of the Virginia Polytechnic Institute (Blacksburg, Va.). The molar absorptivity of this compound is around 750 $M^{-1}$ $cm^{-1}$ at 273 nM (absorption queue, methanol) and was soluble at 0.75 mM in 1% GAB-DMSO buffer.

Observe that the added 273 nm absorptivities of baccatine III and the methyl ester of the side chain were approximately that of paclitaxel. F. Amat-Guerri of the Instituto de Química Orgánica, CSIC (Madrid, Spain) supplied the fluorescent probe Flutax-2; its purity was checked with HPLC and its concentration was determined spectrophotometrically with 0.5% sodium dodecyl sulphate (SDS) at neutral pH, using an extinction coefficient of 49,100 $M^{-1}$ $cm^{-1}$ at 496 nm (Diaz, J. F. et el.).

2. Target: Cross-Linked Microtubules

Tubulin from bovine brain was purified and stored, and its concentration was measured as has been described (Andreu, J. M. et al.). Prior to its use it was balanced in 10 mM sodium phosphate, 1 mM EGTA, 0.1 mM GTP, 3.5M glycerol pH 6.8, with a Sephadex G-25 gravity column used cold, and it was centrifuged cold for 10 min at 50,000 in a TLA 100.4 rotor (Beckman) cold. The 50 μM tubulin was made 6 mM in $MgCl_2$ (in other words, glycerol assembly buffer GAB, final pH 6.5) and 1 mM GTP, it was assembled in microtubules at 37° C. and these were gently cross-linked with 20 mM glutaraldehyde, the reaction being stopped with $NaBH_4$ as has been described (Diaz, J. F. et al.). These cross-linked microtubules have the same specificity, kinetics and stoichiometry for binding to Flutax-2 as the uncross-linked controls, they have a normal morphology under the electron microscope (Diaz, J. F. et al.). The cross-linked microtubules were dialysed against GAB-0.1 mM nucleotide (GTP or GDP) for more than 16 h, cold, in dialysis cassettes (Pierce) and were conserved frozen drop by drop in liquid nitrogen, or at 4° C. with 0.05% of sodium azide. This conservation method for the cross-linked microtubules by means of dialysis against a conservation and cryopreservation buffer is claimed in the present invention.

Their concentration of total tubulin was measured after diluting them in 1% SDS using an extinction coefficient of 107,000 $M^{-1}$ $cm^{-1}$ at 275 nm (Diaz, J. F. and Andreu, J. M.). The concentration of bound tubulin was determined by sedimentation and it was found that it was typically 80-90% of the total. The concentration of binding sites of taxoid was determined by addition of growing concentrations of microtubules cross-linked to 5 µM Flutax-2 in the GAB-GDP buffer, sedimentation (Diaz, J. F. et al., 50,000 rpm in a Beckman TLA 120 rotor at 25° C.) and spectrophotometric measurement of Flutax-2. It was observed that the preparations of cross-linked microtubules bound 0.75±0.05 of Flutax-2 per total tubulin (in other words, a minimum of 95% of the bound tubulin was active binding this ligand). The control measurements using $^3$H-paclitaxel and liquid scintillation gave values similar to Flutax-2. Once the anisotropy values of Flutax bound to microtubule and free were determined, the number of sites could also be determined by valuation of diluted solutions of microtubules cross-linked with Flutax-2 (see further below). The concentration of binding sites of taxoids of the preparations of cross-linked microtubules turned out to be stable in liquid nitrogen, decaying at speeds between 0.02 and 0.05 day$^{-1}$ at 4° C. (mean lives of five and two weeks respectively). The cross-linked microtubules were used within one average life starting from the preparation. A fluorescence micrography of these microtubules with Flutax-2 is shown in FIG. 1.

3. Spectroscopic Measurements of Fluorescence and Anisotropy

Fluorescence spectra were obtained corrected with a Fluorolog-3-221 photon count instrument (Jobin Yvon-Spex, Longlumean, France), with an emission bandwidth of 5 nm and excitation of 1 µm at 25° C. The fluorometric measurements of concentration were made with a Shimadzu RF-540 spectrofluorometer. The anisotropy spectra and measurements were gathered in the Flourolog format-T mode with vertically polarised excitation and were corrected by the sensitivity of each channel with horizontally polarised excitation (Lackowitz, J. R.). The multiple measurements of anisotropy were made with a PolarStar microplate reader (BMG Labtechnologies, Offenburg, Germany) at 25° C. The solutions were excited with 200 pulses of vertically polarised light (band-pass filter 485-P, 480-492 nm ) and the emission was simultaneously analysed with vertical and horizontal polarisation filters (band-pass 520-P, 515-550 nm ). The sensitivity of the two channels was adjusted in order to give an anisotropy value of free Flutax-2 (0.055, polarisation 0.080; GAB buffer at 25° C.) in wells that contained Flutax-2 and not microtubules. The values of well blanks with microtubules and without Flutex-2 were subtracted from the values of fluorescence intensity (the blanks typically represented less than 4% of the measurement).

4. Binding of Flutax to Microtubules

First of all, Flutax-2 (50 µM) was valuated with growing concentrations of binding sites provided by cross-linked microtubules, in GAB buffer at 25 C. The fraction of bound Flutax-2 was:

$$[F]_b/[F]_0 = (r - r_{min})/(r_{max} - r_{min}) \quad [1]$$

where $[F]_b$ and $[F]_0$ are total and bound concentrations of Flutax-2 respectively, r is fluorescence anisotropy measured with the spectrofluorometer, the value of $r_{min}$ is 0.055 and the value of $r_{max}$ was an adjustable parameter. Assuming a one to one binding, the concentration of free binding sites [S] is:

$$[S] = [S]_0 - [F]_b \quad [2]$$

and the following expression is applied:

$$r = r_{min} + (r_{max} - r_{min}) K_0[S]/(1 + K[S]) \quad [3]$$

Equation 3 was iteratively applied in order to fit the data r vs [S] using different starting values of $r_{max}$ in equations 1 and 2, with a program based on the Marquardt algorithm, from which the best fixed value $r_{max} = 0.29$ was obtained. The control measurements with binding sites of microtubules blocked by 10 µM paclitaxel gave values of r very close to $r_{min}$, within an $[S]_0$ interval from 0 to 100 nM. The cross-linked microtubules (50-100 nM of total tubulin) were afterwards valued with known concentrations of Flutax-2. The binding was determined as:

$$[F]_b/[T]_0 = [F]_0 (r - r_{min})/[T]_0 (r_{max} - r_{min}) \quad [4]$$

where $[T]_0$ is the concentration of total tubulin and $r_{max}$ and $r_{min}$ have the previously determined values. The concentration of free Flutax-2 is:

$$[F] = [F]_0 - [F]_b \quad [5]$$

The binding equation for independent sites $$[F]_b/[T]_0 = n K_b [F]/(1 + K_b [F]) \quad [6]$$

was iteratively fitted to the data with a program based on the Marquardt algorithm in order to obtain the best fixed values of n, the number of binding sites of Flutax-2 per total tubulin, and Kb, and the binding equilibrium constant. When these procedures are repeated using the polarisation plate reader, instead of spectrofluorometer, $r_{max}$ values of 0.245 (with Costar 3599 plates) and 0.27 (with Nunc 267342 black plates) were obtained, with values of $K_b$ and n within experimental error.

5. Measurements of Ligand Binding to the Paclitaxel Binding Site of Microtubules by Displacement of Flutax-2

These competitive measurements were made with the polarisation plate reader. A solution of known concentrations of binding sites of microtubule and Flutax-2, both close to 50 nM, in GAB-GDP buffer, was freshly prepared starting from the concentrated reserves of cross-linked microtubules and Flutax-2. It was dispensed in aliquots of 200 µL (final volume) at room temperature in 96-well plates (Costar cat. No. 3599, the wells at the edges were not used). The plates were selected checking that Flutax-2 remained in solution instead of being absorbed onto the polystyrene, measuring the contents of the wells in the spectrofluorometer (90% recovery). The ligands to test were added in small volumes of DMSO (concentration of final DMSO 2% v/v) in order to make the desired duplicated concentrations. A check was also made that the paclitaxel was not adsorbed onto the plate during the test, using $^3$H-paclitaxel and a scintillation counter. The wells without protein and without Flutax-2 were included for calibration and background measurements respectively (see anisotropy measurements, above). The plates were stirred by rotation for 10 minutes and were measured twice within 30-90 minutes following balancing at 25° C. in the microplate reader. The anisotropy data of Flutax-2 was calculated with the evaluation software (BMG) and was traced against the total concentration of the competitor.

With the aim of measuring the binding affinity of a ligand (L) which displaces the reference ligand Flutax-2 from its microtubule binding site (S), unitary stoichiometry was assumed, with the fractional binding of Flutax-2 starting from the anisotropy being determined as $$[F]_b/[S]_0 = [F]_0 (r - r_{min})/[S]_0 (r_{max} - r_{min}) \quad [8]$$

and the following expressions were applied $$K(F) = [SF]/[S][F] \quad [9]$$

$$K(B) = [SB]/[S][B] \quad [10]$$

$$[F] = [F]_0 - [SF] \quad [11]$$

$$[L]=[L]_0-[SL] \quad [12]$$

$$[S]=[S]_0-[SL]-[SF] \quad [13]$$

A personal computer program, which implemented the solutions to equations (9-13) starting from the known values of $[F]_0$, $[L]_0$, $[S]_0$ and $K(F)$ was used to find the best value of fit by means of least squares of the equilibrium binding constant of the competitor ligand $K(L)$ to the data $[F]_b/[S]_0$ versus $[L]_0$ (Medrano, F. J et al.; J. F. Diaz, unpublished program Equigra 4). The fitted displacement curve was expressed as anisotropy and traced together with the data (see FIG. 2).

6. Displacement of $^3H$ Paclitaxel of the Microtubules by Competitor Ligands 100 nM $^3H$ paclitaxel, binding sites of 100 nM microtubules and the desired concentration of competitor in a final volume of 200 μL of GAB-GDP buffer which contained 1 mg mL$^{-1}$ of bovine serum albumin (BSA) and 1% DMSO were incubated for 30 min and centrifuged for 10 minutes at 50,000 rpm, 25° C., in polycarbonate tubes in a TLA 100 rotor with a TLX centrifuge (Beckman, Palo Alto, Calif.). The supernatant fractions and the tubes which contained the sediments were separated and subjected to a count with a liquid scintillation counter. The data were able to be numerically processed in a manner similar to the above section, replacing paclitaxel by Flutax-2.

The invention claimed is:

1. A method for detecting a mimic of paclitaxel in a paclitaxel binding site of a microtubule, comprising:
   (a) providing a target microtubule and a probe wherein the target microtubule is assembled in vitro and stabilized by means of chemical cross-linking and wherein the target microtubule is indefinitely conserved in liquid nitrogen following dialysis against a conservation and cryopreservation buffer,
   (b) adding a test substance to a solution of a target microtubule consisting of said target microtubule and a fluorescent probe bound to the target microtubule,
   (c) determining the drop in anisotropy of said solution at varying test substance concentrations, and
   (d) identifying the test substance as a paclitaxel mimic by means of such drop in fluorescence anisotropy or by measuring the resonance energy transfer to the probe to a suitable acceptor.

2. A method in accordance with claim 1, wherein the probe is a fluorescent derivative of paclitaxel that is specifically bound to a microtubule.

3. A method in accordance with claim 1 wherein the method is robotised and the measurements are made using a fluorescence plate reader.

4. A method in accordance with claim 2 wherein the method is robotised and the measurements are made using a fluorescence plate reader.

5. A method for the high-efficiency (HTP) identification of antitumour compounds acting on a binding site of paclitaxel in a microtubule, deriving from natural or synthetic sources, comprising the steps of the method of claim 1.

6. A method for the evaluation of new derivatives of taxanes, epotilones, discodermalide, eleuterobine, sarcodicitine and any other binding site ligands of paclitaxel in a microtubule, comprising the steps of the method of claim 1.

7. The method of claim 5, for the quantification of the content of said antitumour compounds in a natural production source.

8. The method of claim 6, for the quantification of the content of said new derivatives in a natural production source.

9. A method for the evaluation of new sources for the extraction or preparation of potentially active substances starting from pharmacologically non-active or semi-active precursors, comprising the steps of the method of claim 1.

10. A method for the development of tools for conducting tests in oncological and/or biological research related to cellular microtubules, comprising the method of claim 1.

11. A method in accordance with claim 2, wherein said probe is selected from the group consisting of
   7-O-[N-(2,7-dfluoro-4'-fluoresceincarbonyl)-L-alanyl]paclitaxel,
   7-O-[N-(2,7-dfluoro-4'-fluoresceinsulphonyl)-L-alanyl]paclitaxel,
   7-O-[N-(4'-tetramethylrhodaminrecarbonyl)-L-alanyl]paclitaxel,
   7-O-[N-(2,7-dfluoro-4'-fluoresceincarbonyl)-L-beta-alanyl]paclitaxel.

* * * * *